United States Patent [19]

Saito

[11] Patent Number: 4,708,136

[45] Date of Patent: Nov. 24, 1987

[54] CAUTERY HEMOSTATIC UNIT

[75] Inventor: Tatsuya Saito, Tokyo, Japan

[73] Assignee: Olympus Optical Co., Ltd., Tokyo, Japan

[21] Appl. No.: 11,974

[22] Filed: Feb. 6, 1987

Related U.S. Application Data

[63] Continuation of Ser. No. 774,771, Sep. 11, 1985, abandoned.

[30] Foreign Application Priority Data

Sep. 13, 1984 [JP] Japan ............................ 59-192277
Jan. 11, 1985 [JP] Japan ............................ 60-2700

[51] Int. Cl.⁴ ............................................. A61B 17/36
[52] U.S. Cl. ........................... 128/303.1; 128/303.17; 128/399; 128/400; 403/375; 219/229
[58] Field of Search ........... 128/303.1, 303.11, 303.12, 128/303.17, 343, 399, 400, 401; 403/375; 219/229, 230

[56] References Cited

U.S. PATENT DOCUMENTS 3,118,696 12/1960 Resare .............................. 403/375
3,850,162 11/1974 Iglesias ........................ 128/303.15
4,449,528 5/1984 Auth et al. .................... 128/303.1

Primary Examiner—William E. Kamm
Assistant Examiner—Randy Citrin
Attorney, Agent, or Firm—Armstrong, Nikaido, Marmelstein & Kubovcik

[57] ABSTRACT

This invention is a cautery hemostatic unit which is deliverable through endoscope and used for stopping hemorrhage by cauterizing bleeding wound, is to be attached to the distal extremity of sheath, and forms a gutter-like nozzle which communicates with water channel of the above-mentioned sheath in direction of outer axis of cautery probe wherein a thermal element is incorporated, and the angle of this nozzle is set so that water may be jetted out linearly along the direction of the outer axis of probe. This unit fixes the main unit that composes the above-mentioned probe and a cap with a joint connector which permits freely jointing and disconnecting.

3 Claims, 10 Drawing Figures

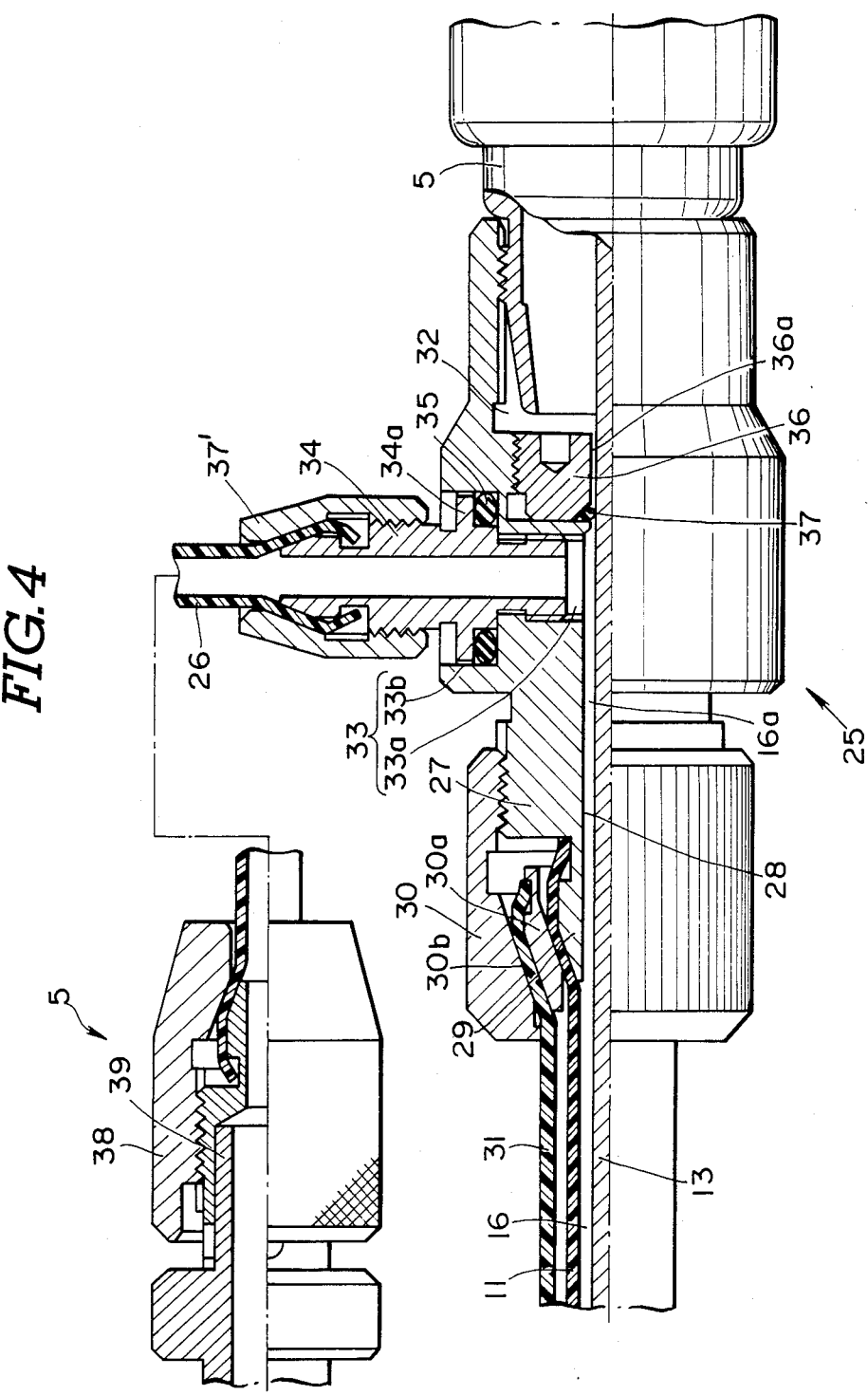

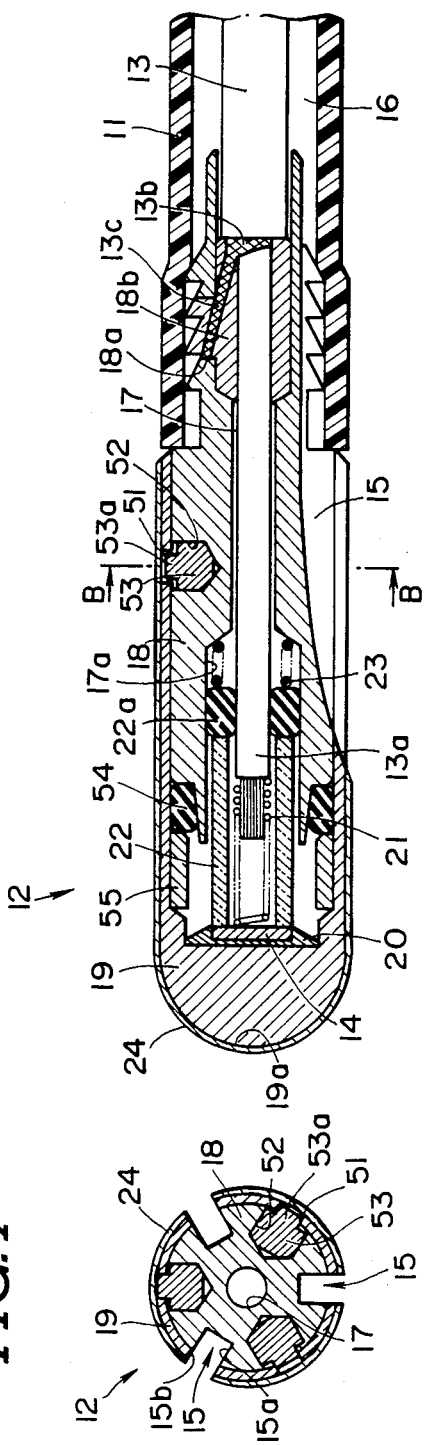
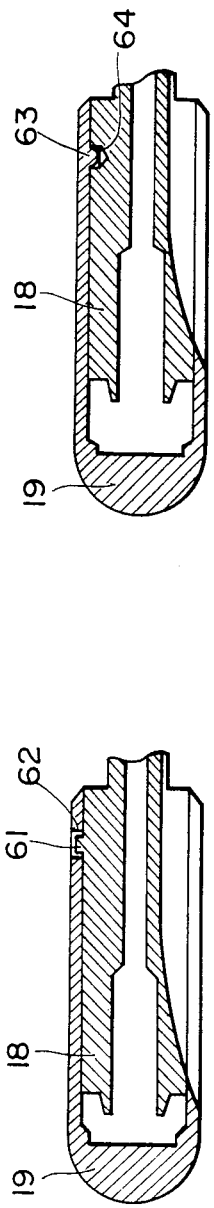
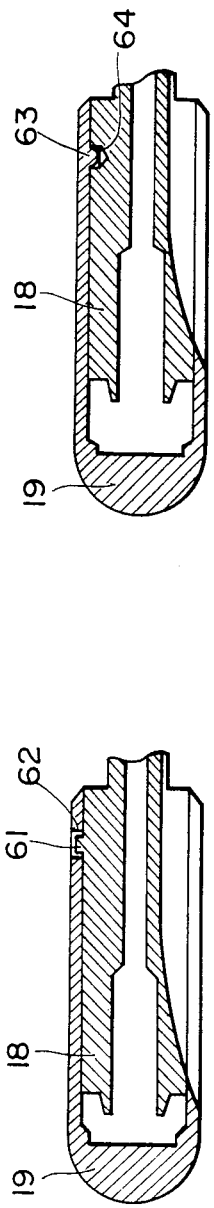

CAUTERY HEMOSTATIC UNIT

This application is a continuation of application Ser. No. 774,771 filed Sep. 11, 1985, now abandoned.

BACKGROUND OF THE INVENTION

1. Field of the Invention

This invention is related to a cautery hemostatic unit which is deliverable through an endoscope and is to be used for stopping hemorrhage by cauterizing a bleeding wound.

2. Related Art Statement

In recent years, endoscopes which permit diagnosing and/or taking therapeutic measures in deep regions of the body, without major incision from the external side of the body, by inserting a slender probe therein, have been used widely in various medical fields.

These endoscopes are designed so that an adequate medical instrument can be inserted into the hollow channel which passes therethrough in order to enable the surgeon to take various therapeutic measures in addition to general observations.

A laser coagulator which irradiates laser beams to coagulate the bleeding site is used as a means to stop bleeding in such cases as removal of a tumor, etc., but the cost is expensive and the use of such a device requires a great deal of skill and, besides, it is highly risky.

For such reasons, an instrument which uses a heater probe which can be delivered therethrough, and which permits coagulating the bleeding site to which this heater probe is applied, by electrically charging a heating coil assembled in the distal extremity of this heater probe, has been developed.

However, such an instrument has a low heat response which does not insure quick heating and subsequent cooling and, thereby, heat penetrates into the surrounding tissues and necrosis of tissues in other sites than the site to be treated may occur until the coagulation is achieved or until the heater probe is cooled after coagulation.

Japanese Patent Application No. 69556/1983 discloses a high-speed heat cautery probe which uses a cautery probe deliverable through a channel in an endoscope and a heater element of good heat response to insure rapid heating and subsequent cooling. This prior art device is equipped with a nozzle to jet out washing solution which is fed through a catheter by pressure, and functions to facilitate the discovery of bleeding by washing blood away from the wound.

However, for the above-mentioned prior art, the composition and shape of the nozzle to jet out washing solution along the direction of outer axis are not published. Besides, this prior art incorporates an electric system to supply electricity to the cautery probe and a water channel to feed washing solution by pressure, but no separate composition of these two channels is taught.

The distal end of the heating cautery probe has a hollow cylindrical cap terminating in a hemispherical surface. The cap is coated with a non-adhesive material and joined by soldering to the end of the slender sheath just distal to the end of the nozzle opening. Because of the proximity of the soldered joint to the end of the nozzle, special care must be exercised to keep solder out of the nozzle.

Furthermore, the non-adhesive coating on the outer surface of the above-mentioned cap will be peeled off gradually by repeated use and the non-adhesive property will eventually be lost. Therefore, it is necessary to regularly recoat the cap with non-adhesive material. However, if non-adhesive coating (for example Teflon coating) is done on the above-mentioned cap without separating it from the probe, the zener diade which is incorporated as heating element therein will be destroyed or damaged because the cautery temperature must be increased above 400° C. For this reason, it is necessary to separate the cap from the probe every time a non-adhesive coating is applied, which, as described, is a tedious process.

SUMMARY OF THE INVENTION

The object of this invention is to offer a cautery hemostatic unit which permits jetting out a washing solution, delivered through a water channel in a slender sheath, linearly along the direction of outer axis of cautery probe so as to feed washing solution ahead of the cautery probe, and to irrigate the bleeding tissues.

Another object of this invention is to provide a cautery hemostatic unit which permits easy replacement of a non-adhesive cap.

Additional object of this invention is to offer a cautery hemostatic unit which makes it possible to position properly the nozzle part of a cap and the nozzle part of a probe, both of which are slotted in the direction of the outer axis.

This invention is arranged to form a slotted nozzle which is attached to the distal extremity of a slender sheath deliverable through a channel in an endoscope and which communicates with a water channel made in the above-mentioned sheath, so as to feed out a washing solution, which is jetted out from the slotted nozzle at an angle of not more than 20° to the direction of the outer axis of cautery probe.

The above-mentioned cautery hemostatic unit is designed so that a hollow cylindrical cap, the outer hemispheric surface of which is coated with non-adhesive coating material and the distal extremity of which is blind, and which is attached to the distal extremity of a sheath wherein a heating element is incorporated, is attached to the cautery be means of connectors that are mounted to them and permit joining and separating freely.

These objects and other objects of the invention will be clarified by the following detailed description.

BRIEF DESCRIPTION OF THE DRAWINGS

FIGS. 1 to 5 are related to the Embodiment 1 of this invention.

In FIG. 1 is a cut-away view of a cautery probe.

FIG. 2 shows the relationship of this probe to its associated equipment.

FIG. 3 is a cross-section taken along line A—A of FIG. 1.

FIG. 4 is a partial interior view showing the electrical connector and the water feed connector that are mounted at the proximal extremity of the sheath.

FIG. 5 is a cross-section of the electrical connector.

FIGS. 6 to 8 are related to the Embodiment 2 of the unit of this invention.

FIG. 6 illustrates the cautery probe.

FIG. 7 shows a cross-section taken along line B—B of FIG. 6.

FIG. 8 is the front view with a partial interior illustration showing the electrical connector and water feed connector that are mounted to the proximal part of the sheath.

FIG. 9 and FIG. 10 show the cross-section of the cap, whereof the interior structure is not illustrated, and the probes that are related to the Embodiments 3 and 4 of the invention.

DETAILED DESCRIPTION

In FIGS. 1 to 5 is shown the first Embodiment of the invention.

Figure 2:
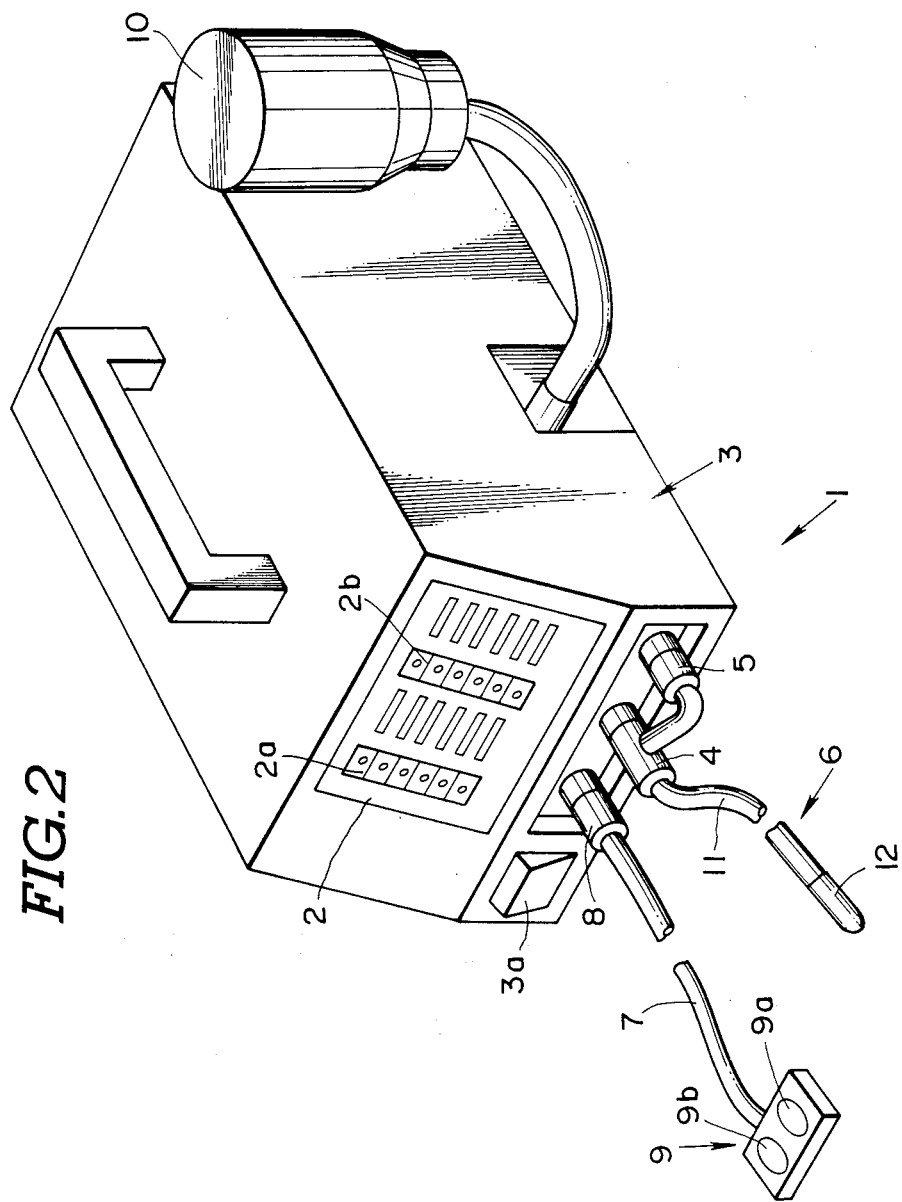

As shown in FIG. 2, the cautery hemostatic unit 1 consists of POWER BOX 3 equipped with CONTROL PANEL 2 on the front thereof, CAUTERY PROBE UNIT 6 which can be freely connected to and disconnected from this POWER BOX 3 by means of ELECTRICAL CONNECTOR 4 and WATER FEED CONNECTOR 5, FOOT SWITCH 9 attached to POWER BOX 3 by means of CONNECTOR 8 mounted to CABLE 7, and WATER TANK 10 that can be freely attached to and detached from POWER BOX 3.

The above-mentioned CAUTERY PROBE UNIT 6 consists of a slender, flexible SHEATH 6, CAUTERY PROBE 12 that is connecter to the distal portion of SHEATH 11, and the above-mentioned ELECTRICAL CONNECTOR 4 and WATER FEED 5 that are mounted to the proximal portion of SHEATH 11 and CAUTERY PROBE attached to the distal portion thereof and which can be delivered through the instrument channel of an endoscope (not shown), through which channel the CAUTERY PROBE 12 can be introduced into the body.

In the above-mentioned SHEATH 11, CO-AXIAL CABLE 13 is inserted in the direction of the axis in order to supply electricity to HEATING ELEMENT 14 that is incorporated in the distal extremity of CAUTERY PROBE 12 and, in the direction of the outer axis of CO-AXIAL CABLE 13 in SHEATH 11, WATER CHANNEL 16 is formed to supply washing water by pressure to plural NOZZLES 15 installed on the outer surface of CAUTERY PROBE 12. After connecting ELECTRICAL CONNECTOR 4 and WATER FEED CONNECTOR 5 at the proximal extremity of CAUTERY PROBE UNIT 6 to POWER BOX 3, connecting FOOTSWITCH 9 to POWER BOX 3 by means of CONNECTOR 8 of CABLE 7, putting MAIN SWITCH 3a of this POWER BOX 3 to "ON" and selecting/setting the heating amount and the water feed amount by the use of HEAT/WATER FEED SETTING BUTTONS on CONTROL PANEL 2, it is possible, by pushing SWITCH 9a of the water feed side of FOOT SWITCH 9, to make the water pump incorporated in POWER BOX 3 feed washing water from WATER TANK 10, via WATER CHANNEL 16 in SHEATH 11, to NOZZLES 15 on the outer surface of CAUTERY PROBE 12 to jet out washing water forwardly to the affected site and to wash away blood from affected site. It is also possible, by pushing SWITCH 9b of the heat side of FOOT SWITCH 9, to supply electricity via CO-AXIAL CABLE 13 in SHEATH 11 to HEATING ELEMENT 14 incorporated in CAUTERY PROBE 12 to heat it to required temperature.

The above-mentioned POWER BOX 3 has an electric system as a power source for cauterization and a water feed system to supply washing water, and these two systems are preferrably isolated from each other by a separating chassis, which separates the inside of POWER BOS 3 horizontally or vertically, in order to assure the safety of the operator. The manufacturing process is also simplifed so that it can be completed by unifying these two systems which can be assembled separately from one another.

Figure 1:
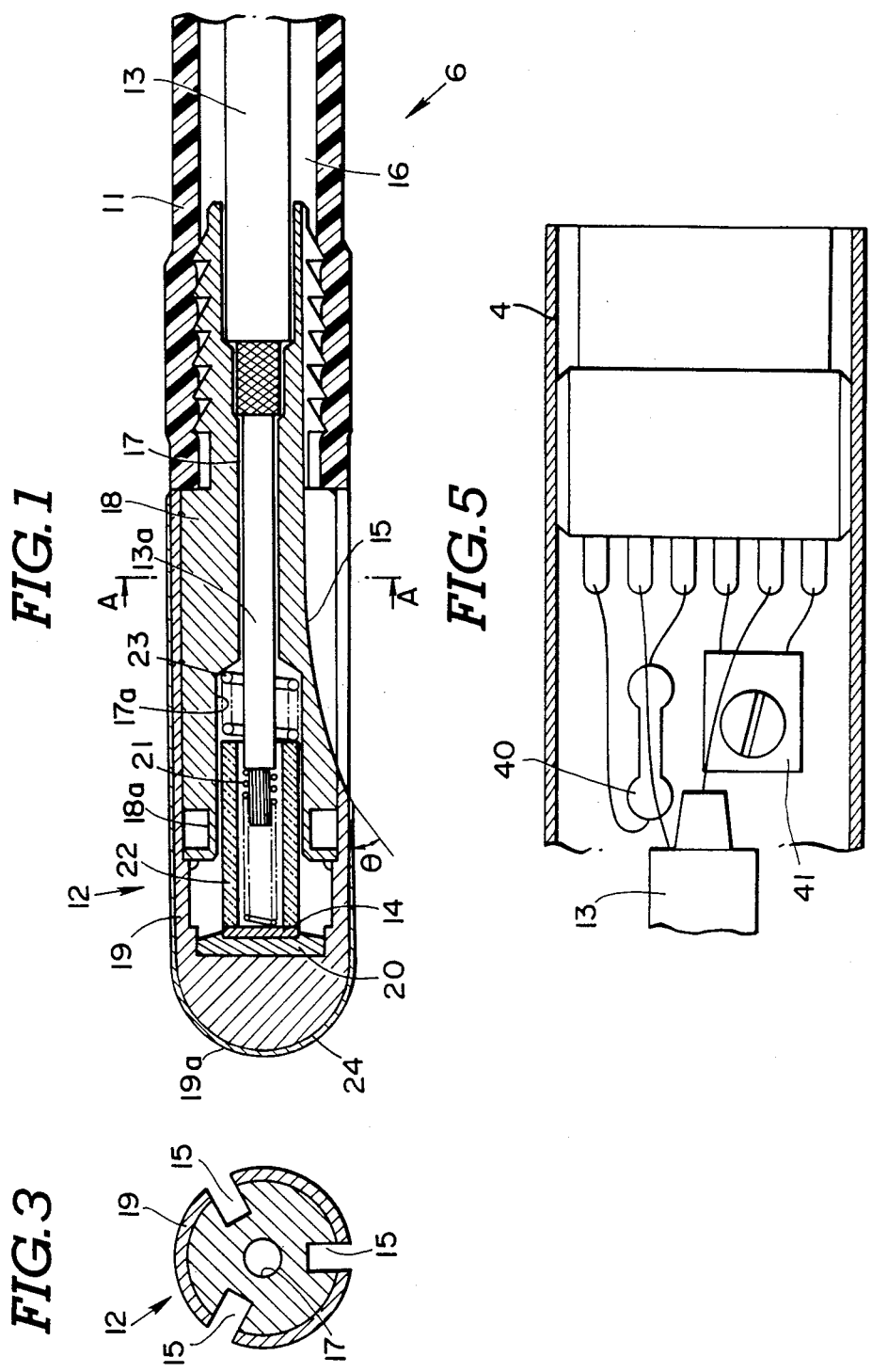

Illustrated in FIG. 1 and FIG. 3 is the detail of CAUTERY PROBE 12 that is attached to the distal extremity of the above-mentioned CAUTERY PROBE UNIT 6. The main part 18 that has THROUGH-HOLE 17 made in the direction of the central axis is fixed to the distal extremity of slender flexible SHEATH 11, for example a Teflon sheath, and to the outer side, a hollow cylindric CAP 19 of good heat conductivity, having a hemispherical end, which is a good heat conduction surface for cauterizing a bleeding wound to which the probe is applied.

On the side of the distal extremity of the main part 18, there is a CONCAVITY 17a which communicates with THROUGH-HOLE 17, and wherein the extremity of CO-AXIAL CABLE 13 inserted from the side of SHEATH 11 is positioned. To the inner wall opposite to the hemispheric heat conduction surface 19a of CAP 19, a heating element 14 such as a Zener diode is joined by solder 20, and CO-AXIAL CABLE 13 and HEATING ELEMENT 14 are connected electrically to each other by FEED COIL 21. HEATING ELEMENT 14 is held in contact, via an isolation tube such as a glass tube, with the soldered side 20 by COIL SPRING 23, one end of which directly contacts an inner wall of CONCAVITY 17 to prevent the movement of HEATING ELEMENT 14 due to melting of the solder which fixes the heating element. Since HEATING ELEMENT 14 is contacted with the soldered side 20 by COIL SPRING 23 as mentioned above, CORE WIRE 13a of CO-AXIAL CABLE 13 and HEATING ELEMENT 14 are connected to each other by way of CURRENT SUPPLY COIL 21. CAP 19, having a hemispherical heat conduction surface 19a at the extremity thereof, is coated with non-adhesive coating 24, for example Teflon coating, in order to prevent CAP 19 from adhering to the tissue to which it is applied. This is to prevent possible reopening of the cauterized wound when the cautery is removed. Non-adhesive coating 24 is coated on the outer surface of the above-mentioned CAUTERY PROBE 12 separately from CAP 19, and, therefore, CAP 19 is attached to HEATING ELEMENT 14 and the body 18 after non-adhesive coating 24 has been applied to CAP 19. This assures no breakdown or damage to HEATING ELEMENT 14. However, according to the prior art, a non-adhesive coating is applied after attaching the hemispheric head to the main body 18. Breakdown or damage to HEATING ELEMENT 14, such as a Zener diode occurs when the temperature of non-adhesive coating is raised to 400° C. or above during application of the coating.

NOZZLES 15 of the above-mentioned CAUTERY PROBE 12 are formed on the linear part of the main body 18 and CAP 19. These NOZZLES 15 are formed slot-like in the direction of the outer axis and the posterior end thereof communicates linearly with WATER CHANNEL 16 that is formed in SHEATH 11. The outlet side is sloped gently at an angle of 15°–16°. The distance between the outlet of nozzle and the distal extremity of PROBE 12 is set to be not less than the curvature radius of the hemispheric heat conduction surface 19a of PROBE 12. That NOZZLES 15 are formed as mentioned above makes is possible to lead washing water, which is jetted out from NOZZLES 15, linearly along the direction the the outer circular axis and to feed it linearly ahead of PROBE 12. Thus it is available to wash easily the point to be washed and to prevent the return of washing water to the inside of the hemispheric heat conduction surface. The main body 18 also has a heat radiation slot 18a for cooling.

ELECTRICAL CONNECTOR 4 and WATER FEED CONNECTOR 5 mounted on the proximal side of the above-mentioned CAUTERY PROBE UNIT 6 are composed as shown in FIG. 4 and FIG. 5. Joint part 25 of the water feed tube is connected to the posterior end of SHEATH 11, and ELECTRICAL CONNECTOR 4 is connected to the posterior end of joint part 25 and the WATER TUBE 26 is connected to a lateral side of joint part 25, and at this position the electricity system and the water channel system are separated from each other and from this position CO-AXIAL CABLE 13 and WATER CHANNEL 16 enter SHEATH 11. The main body 27 of the above-mentioned joint part 25 has a through-hole 28 made in the direction of the central axis to deliver CO-AXIAL CABLE 13, which comes from the SHEATH 11 side forward to ELECTRICAL CONNECTOR 4.

A taper-formed joint 29 is projecting ahead of main body 27 and the posterior end of SHEATH 11 is connected to joint 29. A male screw thread is formed on the posterior outer circumference of joint 29, and a stop ring 30, which has a taper-formed press ring 30a on the inner circumference, is screwed to the male screw thread in order to fix the posterior end of SHEATH 11 by pressing it against ring 30. Between the taper-formed press ring 30a located on the inner circumference of stop ring 30 and the inner circular surface of stop ring 30 there is a ring-formed slot 30b wherein the posterior end of breakage-preventive tube 31 that is mounted on the exterior of the proximal side of SHEATH 11 is fixed. On the side of the posterior end of main body 27 is a concavity 32 which communicates with THROUGH-HOLE 28, and a female screw thread is formed on the inner circular surface of this concavity 32 whereto ELECTRICAL CONNECTOR 4, which has a male screw thread on its distal extremity, is connected. Furthermore, this main body 27 has a two-stepped concavity 33 which communicates with the above-mentioned THROUGH-HOLE 28, and a female screw thread is formed in the smaller-diameter concavity 33a of concavity 33, whereto JOINT 34 of WATER TUBE 26 is screwed. Between FLANGE 34 located on the exterior of JOINT 34 and the bottom of the larger concavity 33b, an O-ring 35 is placed to prevent leakage of water. Thus, WATER TUBE 26 communicates with THROUGH-HOLE 28 of the main body 28 of joint part 25 via JOINT 34, and the space between CO-AXIAL CABLE 13 passing through THROUGH-HOLE 28 and the inner wall surface thereof is utilized as WATER CHANNEL 16a, and this channel communicates with WATER CHANNEL 16 of SHEATH 11 which is joined to the main body 27 of the joint part. On the bottom of CONCAVITY 32, is a female screw thread whereto press-screw 36, which has a through-hole 36a for co-axial cable is fixed, and an O-ring 37 is located between the distal end of this press-screw 36 and the outer circumference of CO-AXIAL CABLE 13 or the above-mentioned through-hole 28, and this O-ring 37 is pressed with a press-screw 36 between the side of WATER CHANNEL 16a and the side of ELECTRICAL CONNECTOR 4, which insures the isolation of the electric system and the water channel system from each other.

The above-mentioned WATER TUBE 26 and JOINT 34 are connected to each other with a taper screw 37.

CONNECTOR 5, mounted on the posterior end side of this WATER TUBE 26, has a locking socket 38 and can be freely connected to and disconnected from WATER FEED PLUG 39 of POWER BOX 3.

Into ELECTRICAL CONNECTOR 4, connected to the posterior end of the main body 27 of the above-mentioned joint part, CO-AXIAL CABLE 13 is connected to a contact point via FIXED RESISTANCE 40 and VARIABLE RESISTANCE 41. A variable resistance 41 is located so that a constant current can be supplied without being influenced by variation in Zener voltage of Zener diode HEATING ELEMENT 14, or by variation in resistance of the cable 13, and this variable resistance 41 permits adjusting easily current value and improving work efficiency.

Figure 8:
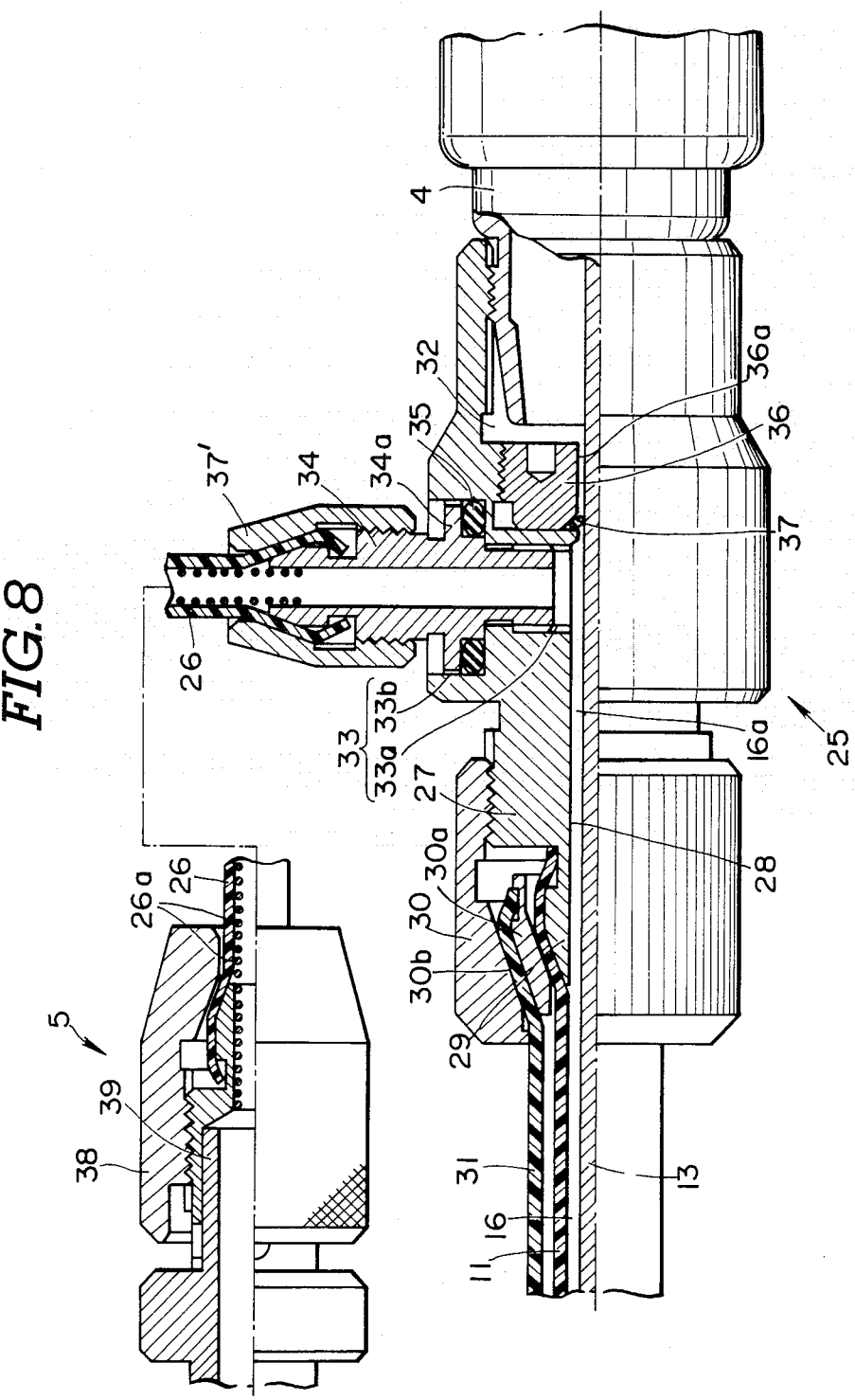

In FIGS. 6 to 8 is shown the second Embodiment of this invention. In this embodiment, the main body 18 that composes CAUTERY PROBE 12 and CAP 19 can be freely connected to each other by a joint part. On the outer circumference of CAP 19 and the main body 18, except at NOZZLES 15, joint hole 51 and pin implant hole 52 are formed at trisection points in order to implant PIN 53 (which has a projection 53a) in pin implant holes 52. Projection 53a is inserted into joint hole 51 of CAP 19 to hold CAP 19 to the outer circumference of main body 18. So as a result, CAP 19 can be freely connected to the main body 18. Therefore, in this constitution, by joining CAP 19 to the main body 18 and by connecting the projection 53a of PIN 53 to joint hole 51 of CAP 19, slot 15b of CAP 19 and slot 15a of the main body 19 that constitute the above-mentioned NOZZLES 15 are connected to each other in proper position.

Between the distal extremity of the above-mentioned main body 18 and CAP 19, O-ring 54 is pressed against the main body 18 side with a ring-formed O-ring press material 55 so that one extremity is in contact with the main body 18 side. This O-ring press material 55 is also used as an O-ring guide to insert the distal extremity of the main body 18 into CAP 19 by pushing O-ring 54 into CAP 19 on the side when CAP 19 is fixed.

In this embodiment, between ISOLATION TUBE 22, such as a glass tube, whereof the one edge is in contact with HEATING ELEMENT 14, and COIL SPRING 23, O-ring 22a is used to seal against water which infiltrates therein along CO-AXIAL CABLE 13 from the side of SHEATH 11.

Furthermore, OUTER WIRE 13b of the above-mentioned CO-AXIAL CABLE 13 forms a twist part 13c at the distal end thereof, and this twist part 13c is connected to the main body 18 by solder 18b which fills fixations hole 18a at the posterior part of main body 18. In addition, as shown in FIG. 8, COIL 26a, which is mounted in WATER FEED TUBE 26, functions to prevent breakage of WATER FEED TUBE 26 and to improve the bend resistance thereof.

Otherwise, the constitution of Embodiment 2 is similar to that of Embodiment 1.

In FIG. 9 is shown Embodiment 3, which is directed to the connection of the cap and the main body of this invention. In this embodiment, the main body 18 has a projection 61 on its outer circumference to join into hole 62 made on CAP 19.

In FIG. 10 is shown Embodiment 4, which is directed to the joint of the cap and the main body of the invention.

In this embodiment, a projection 63 is formed on the inner circumference of CAP 19. A joint hole 64 is formed at a position on the outer circumference of the main body, which corresponds to the position of the projection 63, and this projection 63 of the above-mentioned CAP 19 is inserted and fixed in the joint hole 64 of the main body 18.

It is also contemplated to form a female screw thread on the inner circumference of the cap and a male screw thread on the outer circumference in order to secure the cap. In this case, the screws are formed so that, when the cap is fixed, the slit of the cap will correctly communicate with the slot of the main body to form a nozzle.

This invention also encompasses various embodiments obvious to the art-skilled person without deviating from the spirit and field of the invention.

I claim:

1. A cautery hemostatic unit deliverable through a tool channel of an endoscope comprising:
   (a) a tubular main body part having proximal and distal ends attached at its proximal end to a flexible sheath, said main body part having a through-hole in the direction of the central axis and a plurality of slotted longitudinal channels formed on the outer surface of the main body;
   (b) an electrically energized heating means inserted into said through-hole at the distal end of said main body part;
   (c) a tubular cap having a closed, hemispherical end and a plurality of slots open to the proximal end corresponding in number and radial position to said slots on said main body part, said cap having a non-adherent outer coating and an inner diameter sized so as to fit snugly over the distal portion of said main body part;
   (d) means for detachably securing said cap on said main body part;
   (e) means for electrically connecting said heating means to an external controller through said main body part and said sheath; and
   (f) means for delivering a non-toxic liquid through said sheath to said slots in said main body part wherein said slots on said main body part terminate distally, with a gentle slope to the surface of the main body, at a point not less than the radius of curvature of the hemispherical portions of said cap from the distal extremity of the cap, said slope having an angle of curvature which directs said non-toxic liquid at an angle of not more than 20° to the longitudinal axis of said main body.

2. A cautery hemostatic unit according to claim 1 wherein the means for detachably securing said cap to said main body part comprises a fixed pin inserted into an implant hole formed in the surface of said main body, said pin having a projecting portion means for insertion into an engaging notch formed on the inner surface of said cap when said cap is slid over the end of said main body part.

3. Cautery hemostatic unit of claim 2 wherein the securing means comprises a projection on the cap and a joint hole on the main body.

* * * * *